United States Patent [19]

Albino et al.

[11] Patent Number: 5,009,995

[45] Date of Patent: Apr. 23, 1991

[54] MONOCLONAL ANTIBODIES TO MELANOMA CELLS

[75] Inventors: Anthony Albino, New York; Kenneth Lloyd, Bronx, both of N.Y.; Hisami Ikeda, Asahikawa, Japan; Lloyd Old, New York, N.Y.

[73] Assignee: Sloan-Kettering Institute for Cancer Research, New York, N.Y.

[21] Appl. No.: 166,660

[22] Filed: Mar. 11, 1988

Related U.S. Application Data

[63] Continuation of Ser. No. 924,144, Oct. 27, 1986, which is a continuation of Ser. No. 481,378, Apr. 1, 1983, abandoned.

[51] Int. Cl.$^5$ .................. G01N 33/535; C07K 15/28; C12N 5/18; A61K 39/00
[52] U.S. Cl. .................................. 435/7.23; 530/387; 530/388; 435/240.27; 435/70.21; 435/172.2; 424/85.8; 424/85.91; 436/548
[58] Field of Search .............................. 530/387, 388; 435/240.27, 68.7; 424/85.8, 85.91; 436/548; 935/100, 104, 107, 108, 110

[56] References Cited

U.S. PATENT DOCUMENTS

| | | | |
|---|---|---|---|
| 4,172,124 | 10/1979 | Koprowski et al. | 424/85.8 |
| 4,331,647 | 5/1982 | Goldenberg | 424/1.1 |
| 4,414,148 | 11/1983 | Jansen et al. | 260/112 |

OTHER PUBLICATIONS

Dippold et al., British J. Cancer 43:561, 1981.
Sahu et al., Inflammation 3:437–445, 1979.
Bystryn et al., J. Nat'l. Cancer Inst. 52:1263-9, 1974.
Albino et al., J. Immunol. 13(3): 1595-99, Sep. 1983.
Bumol et al., Hyb. Cell Imortal. (Proc. Nat'l. Symp. 1981); pp. 171-184, Baldwin T., ed. Plenum, N.Y. 1983.
Dippold et al., PNAS, U.S.A. 77:6114-8, Oct. 1980.
Lakin et al., J. Neurochem. 37: 1170-8, 1981.

*Primary Examiner*—Esther L. Kepplinger
*Assistant Examiner*—Paula Hutzell
*Attorney, Agent, or Firm*—John P. White

[57] ABSTRACT

This invention relates to monoclonal antibodies recognizing the gp130 antigen of human cells. Monoclonal antibodies which recognize distinct determinants on this antigen and methods of detecting the determinants by immunoassay with the monoclonal antibodies which recognize them are disclosed. The monoclonal antibodies are useful in the detection of the gp130 antigen and human cells including melanoma which contain this antigen.

7 Claims, No Drawings

MONOCLONAL ANTIBODIES TO MELANOMA CELLS

This present invention was wholly or partially made with funds provided by the Department of Human Health and Services under Grant No. CA-08748, CA-19765 & CA-21445. Accordingly, the United States Government has certain rights in this invention.

This application is a continuation of U.S. Ser. No. 924,144, filed Oct. 27, 1986, now abandoned which is a continuation of U.S. Ser. No. 481,378, filed Apr. 1, 1983, now abandoned.

This invention relates to an antigen found on human melanoma cells and to antibodies which recognize this antigen. The use monoclonal antibodies in the diagnosis and of melanoma is given.

BACKGROUND

Serological analysis using mouse monoclonal antibodies has identified a number of cell surface antigens expressed on cultured human melanoma cells (Dippold, W. G., K. O. Lloyd, L. T. C. Li, H. Ikeda, H. F. Oettgen and L. J. Old. 1980, *Proc. Nat'l Acad. Sci., U.S.A.* 77:6114; Houghton, A. N., M. Eisinger, A. P. Albino, J. G. Cairncross and L. J. Old, 1982, *J. Exp. Med.* 156:1755; Albino, A. P., K. O. Lloyd, A. N. Houghton, H. F. Oettgenand L. J. Old, 1981, *J. Exp. Med.* 154:1764)). The ink products of the major histocompatibility complex B, C and D loci) and a variety of differentiation antigen. The detailed structure of most of these antigens, as well their biological functions, remains to be elucilated.

One glycoprotein of 130,000 molecular weight (gp130), first defined by Dippold et al. (Dippold, W. G., K. O. Lloyd, L. T. C. Li, H. Ikeda, H. F. Oettgen and L. J. Old, Supra, and designated gp150, was shown to be present in greatest amounts on cultured human melanoma lines (40/43) and cultures of astrocytoma (7/10) and to a lesser degree on a wide range of other malignant or normal cell types.

The potential usefulness of this antigen in the diagnosis and treatment of melanoma has led to efforts toward further elucidation of its biochemical and immunochemical behavior.

SUMMARY

This invention relates to monoclonal antibodies recognizing the gp130 antigen of human cells. Monoclonal antibodies which recognize distinct determinants on this antigen and methods of detecting the determinants by immunoassay with the monoclonal antibodies which recognize them is disclosed. Hybridoma cell lines which produce the monoclonal antibodies of the present invention are also disclosed. The monoclonal antibodies are useful in the detection of the gp130 antigen and human cells including melanoma which contain this antigen

DESCRIPTION

Availability of Hybridoma Cell Lines

The hybridoma lines disclosed in the present invention bear the designated deposit number and are deposited with Sloan-Kettering Institute, 1275 York Avenue, New York, N.Y, 10021. Preferred cell lines of the present invention are also deposited at the Patent Culture Depository of the American Type Culture Collection 12301 Parklawn Drive, Lockville Md. U.S.A., and bear the following deposit numbers

| Sloan-Kettering Deposit # | ATCC # |
|---|---|
| 846 | |
| 239 | HB8288 |
| 986, 35 | HB9284 |
| 829 | HB8289 |

Hybridoma cell line 986.35 was deposited on Nov. 21, 1986 pursuant to, and in satisfaction of the Requirements of the Budapest Treaty on the International Recognition of Microorganisms for the Purposes of Patent Procedure. The hybridoma cell line MA6 829/NS. 1 was originally deposited with the ATCC as a national deposit on Mar. 31, 1983 and was subsequently converted, on Sept. 4, 1987, to satisfy the requirements of the Budapest Treaty on the International Recognition of Microorganisms for the Purposes of Patent Procedure Deposit is for the purpose of enabling disclosure only and is not intended to limit the concept of the present invention to the particular materials deposited.

PREPARATION OF MONOCLONAL ANTIBODIES

Tissue culture. Melanoma and other cell lines were derived as described previously (Albino, A. P., K. O. Lloyd, A. N. Houghton, H. F. Oettgen and L. J. Old, Supra; Carey, T. E., T. Takahashi, L. A. Resnick, H. F. Oettgen and L. J Old, 1976, *Proc. Nat'l. Acad. Sci., U.S.A.*, 73:3278; Ueda, R., H Shiku, M. Pfreundschuh, T. Takahashi, L. T. C. Li, W. F. Whitmore, Jr., H. F. Oettgen and L. J. Old, 1979, *J. Exp. Med.* 150:564). B cell lines were derived from virus (EBV) from the B.95.8 marmoset lymphoid line. Cultures were maintained in Eagle's minimum essential medium supplemented with 2 mM glutamine, 1% non-essential amino acids, 100 U/ml penicillin, 100 $\mu$g/ml streptomycin, and 10% fetal bovine serum (FBS)

Serological procedures. The protein A-mixed hemadsorption (PA-MHA) and anti-mouse IgG-MHA assays were performed as previously described (Albino, A. P., K. O. Lloyd, A. N. Houghton, H. F. Oettgen and L. J. Old, 1981, Supra. Target cells (plated 1-2 days previously) and mouse monoclonal sera were incubated for 1 hr at 37° C. After washing the target cells, indicator cells were added and incubated with target cells for 1 hr. The plates were then washed gently and reactions evaluated under light microscopy. Qualitative absorption tests were performed by absorbing 30-50 $\mu$l of serum (diluted according to the endpoint) with an equal volume of washed packed cells for 1 hr at room temperature for residual antibody on target cells grown in Falcon 3034 plates (Falcon Plasticware).

Immunization. (BALB/c$\times$C57BL/6)F$_1$ female mice were immunized with SK-MEL-28, an established melanoma cell line by seven immunizations over a 7-month interval with increasing number of cells. For the initial immunization, $2\times10^6$ melanoma cells were injected subcutaneously with Freund's complete adjuvant. The mice are further immunized at 4-week intervals by intraperitoneal inoculation of melanoma cells. The final immunization consisted of $50\times10^6$ melanoma cells, injected intraperitoneally and intravenously. Other mice were immunized with a soluble antigen preparation consisting of a papain-digest of SK-MEL-28 (Carey, T. E., K. O. Lloyd, T. Takahashi, L. R. Travassos and L. J. Old, 1979, Proc. Nat'l. Acad. Sci., U.S.A. 76:2898)) which was subsequently fractionated by concanavalin A-Sepharose and subtractive affinity chromatography on a mouse anti-HLA (W6/32)-Sepharose column.

Production of mouse monoclonal antibodies. The fusion of immune spleen cells with mouse myeloma MOPC-21 NS-1 cells (ratio - 5-10:1) was performed as described (Dippold, W. G., K. O. Lloyd, L. T. C. Li, H. Ikeda, H. F. Oettgen and L. J. Old, Supra. Antibody subclass was determined by double diffusion in agar with anti-Ig heavy chain-specific reagents. Cultures of cloned hybridomas were injected subcutaneously into nu/nu (athymic) mice (NIH/Swiss background). Sera from mice with progressively growing tumors were used for serological and biochemical characterization.

Production of F(ab')$_2$ antibody fragments. Monoclonal antibody 846 was purified by the procedure of Ley et al. (Ey, P. L., S. J. Prowse and C. R. Jenkin, 1978, Immunochem. 15:429). Briefly, 3 ml of mouse ascites fluid was mixed with 3 ml of 0.1M sodium phosphate, pH 8.0 and adjusted to pH 8 1, with 1M Tris HCl, pH 9.0. This sample was then applied to a column packed with 5 ml of protein A-Sepharose 4B (Sigma Chemical Co., St Louis, Mo.), and pre-equilibrated with 0.1 sodium phosphate, pH 8.0 at 4° C. The 846 IgG antibody was eluted from the column with 50 ml 0.1M sodium citrate, pH 6.0. This solution was dialyzed against two liters of 0.1M sodium acetate, pH 4.1 and the solution containing 5 mg IgG$_1$ antibody was then reduced to a volume of 2 ml by pressure dialysis in an Amicon chamber. Pepsin (300 $\mu$g) was then added and the solution was incubated for 16 hours at 37° C. The solution was neutralized with 0.1N NaOH to a final pH of 8.0, then passed over a 5 ml column of protein A-Sepharose 4B (see above), to remove any intact immunoglobulins. The nonabsorbed flow-through was collected and tested for residual reactivity with protein A to show that all protein A-binding activity had been removed. F(ab')$_2$ fragments of 846 monoclonal antibody were stored at $-20°$ C. until needed.

Radioiodination. 846 antibodies were labeled with $^{125}$I using the procedure of Hunter and Greenwood (Hunter, M. M. and F. C. Greenwood, 1982. Nature 194:495). Protein A-purified 846 IgG antibody (50 $\mu$g) was labeled with 1 mCi $^{125}$I and separated from unbound $^{125}$I on a biogel P-30 column.

Immunoprecipitation procedures. SK-MEL-28 cells were labeled as follows: (i) metabolic incorporation of [$^{35}$S]methionine (Amersham, 1000 Ci/mmol; 1 Ci=$3.7 \times 10^{10}$ becquerels) by using 250 $\mu$ Ci in 10 ml of methionine-free minimal essential medium (MEM) containing 1% fetal bovine serum (FBS) for 16 hours and (ii) metabolic incorporation of [$^3$H]glucosamine (30–60 Ci/mmol) by using 150 $\mu$ Ci in 10 ml of minimal essential medium with 10% (vol/vol) FBS for 72 hrs. Labeled cells were extracted with 0.1% Nonidet P-40 in 0.15M NaCl/0.01M Tris, pH 7.2 (Tris buffer) containing 0.1 mM phenylmethylsulfonyl fluoride, and the solution was clarified by centrifugation at 100,000$\times$g and filtered through a 0.22-$\mu$m filter. Immunoprecipitation was carried out by mixing a portion of the cell extract (5–10$\times$10$^5$ cpm) with 5 $\mu$l of mouse antibody, 15 $\mu$l of rabbit anti-mouse Ig (Cappel Laboratories, Cochranville, Pa.) serum, and 500 $\mu$l of 0.1% Nonidet P-40 in Tris buffer with 1% gammaglobulin-free FBS. Before use, cell extracts (0.1–1 ml) were precleared with 5 $\mu$l of normal mouse serum, 15 $\mu$l of rabbit anti-mouse Ig and 200 $\mu$l of 10% (wt/vol) *Staphylococcus aureus* suspension. Immune complexes were isolated by using *S. aureus*, and the labeled components were detected by sodium-dodecyl- sulfate/polyacrlyamide gel electrophoresis and fluorography as described (Dippold, W. G., K. O. Lloyd, L. T. C. Li, H. Ikeda, H. F. Oettgen and L. J. Old, Supra.

Pulse-labeling procedures. SK-MEL-28 cells in logarithmic phase of growth were cultured with 10 ml of methionine-free MEM at 37° C. for 60 min. This medium was then removed and duplicate plates of cells were incubated at 37° C. for 15 min. The medium was removed and the plates of cells were incubated with 3 ml of the same medium plus 100-200 [$^{35}$S]methionine and incubated at 37° C. for 15 min. The medium was removed and the plates washed two times with cold MEM, when re-fed with prewarmed MEM plus 10% FBS. After varying chase periods, the cells were washed twice in cold phosphate-buffered salone (PBS) and lysed with 0.5% Nonidet P-40/0.5% deoxycholate in 0.05M NaCl/0.02 M Tris, pH 7.4 containing 0.2 mM phenyl-methylsulfonyl fluoride. The solution was clarified at 10,000$\times$g and the supernatant was used for immunoprecipitation reactions as described above.

Endo. H treatment. SK-MEL-28 cells were pulse-labeled for 15 min and chased for 60 and 4.5 hours. The cells were washed and lysed, and the resulting supernatants were reacted with the 846 monoclonal antibody. After immunoprecipitation, the resulting immune complexes were dissociated in 1% SDS/0.005M Tris HCl pH 5.5. The supernatants were diluted to 0.2% SDS with 50 mM Tris HCl pH 5.5 and divided into two fractions. One set (i.e., the 15 min pulse, the 15 min pulse with a 60 min chase, and the 15 min pulse with a 4.5 hr chase) received 2 mU Endo- -N-acetylglucosamidase (endo-H) and was incubated at 37° C. for 5 hrs. A duplicate set received the same treatment but without the addition of any enzyme. After incubation, 5 g dithiothreitol was added to each tube which was then heated at 100° C. for 2 min and analyzed on a 7.5% SDS-polyacrylamide gel.

TABLE I

CHARACTERIZATION OF FOUR MOUSE MONOCLONAL ANTIBODIES DETECTING gp130

| CELLS | 846 Titer $\times$ 10$^{-3}$ | Abs. | 239 Titer $\times$ 10$^{-3}$ | Abs. | 829 Titer $\times$ 10$^{-3}$ | Abs. | 986 Titer $\times$ 10$^{-3}$ | Abs. |
|---|---|---|---|---|---|---|---|---|
| Melanomas: | | | | | | | | |
| SK-MEL-13 | 1500 | + | 1500 | + | 1000 | + | 500 | + |
| -28 | 1500 | + | 1500 | + | 1500 | + | 500 | + |
| -29 | 1500 | + | 1500 | + | 1500 | + | 500 | + |
| -37 | 1500 | + | 1500 | + | 1000 | + | 200 | + |
| -75 | 1500 | + | 1000 | + | 1000 | + | 1000 | + |
| -90 | 1000 | + | 1000 | + | 500 | + | 200 | + |
| -113 | 1500 | + | 1500 | + | 500 | + | 250 | + |

TABLE I-continued
CHARACTERIZATION OF FOUR MOUSE MONOCLONAL ANTIBODIES DETECTING gp130

| CELLS | 846 Titer × $10^{-3}$ | Abs. | 239 Titer × $10^{-3}$ | Abs. | 829 Titer × $10^{-3}$ | Abs. | 986 Titer × $10^{-3}$ | Abs. |
|---|---|---|---|---|---|---|---|---|
| -117 | 1500 | + | 1000 | + | 500 | + | 125 | + |
| -119 | 1500 | + | 1500 | + | 1500 | + | 125 | + |
| -129 | 1500 | + | 1500 | + | 500 | + | 50 | + |
| -131 | 1500 | + | 1500 | + | 500 | + | 50 | + |
| -133 | 1500 | + | 1000 | + | 500 | + | 1000 | + |
| -149 | 1500 | + | 1500 | + | 1000 | + | 500 | + |
| -41 | 1500 | + | 1500 | + | 1000 | + | 10 | + |
| -63 | 1000 | + | 1000 | + | 1000 | + | 10 | + |
| -64 | 1000 | + | 1000 | + | 1000 | + | 20 | + |
| -73 | 1500 | + | 1500 | + | 1500 | + | 10 | + |
| -87 | 1500 | + | 1000 | + | 200 | + | 10 | + |
| -93 | 1500 | + | 1500 | + | 1500 | + | 250 | + |
| -61 | 0 | — | 0 | — | 0 | — | 0 | — |
| -72 | 0 | — | 0 | — | 0 | — | 0 | — |
| -78 | 0 | — | 0 | — | 0 | — | 0 | — |
|  | 0 | — | 0 | — | 0 | — | 0 | — |
| Neuroblastomas | | | | | | | | |
| SK-NSH | 1500 | + | 1500 | + | 1500 | + | 250 | + |
| SK-NMC | 1500 | + | 1500 | + | 1500 | + | 1500 | + |
| Astrocytomas | | | | | | | | |
| U251→ | 1500 | + | 1500 | + | 1500 | + | 150 | + |
| SK-MG-4 | 100 | + | 50 | + | 50 | + | 5 | +/— |
| SK-MG-7 | 0.5 | +/— | 0.5 | +/— | 0 | — | 0 | — |
| SK-MG-1 | 0 | — | 0 | — | 0 | — | 0 | — |
| C-12 fetal brain | 0.4 | + | 0.05 | + | 0.05 | + | 0 | — |
| Renal Cancer: | | | | | | | | |
| SK-RC-6 | 20 | + | 20 | + | 2 | +/— | 0 | — |
| SK-RC-1 | 10 | +/— | 10 | +/— | 1 | +/— | 0 | — |
| Caki-1 | 5 | — | 5 | — | 1 | — | 0 | — |
| SK-RC-2 | 0 | — | 0 | — | 0 | — | 0 | — |
| SK-RC-7 | 0 | — | 0 | — | 0 | — | 0 | — |
| SK-RC-8 | 0 | — | 0 | — | 0 | — | 0 | — |
| SK-RC-9 | 0 | — | 0 | — | 0 | — | 0 | — |
| SK-RC-28 | 0 | — | 0 | — | 0 | — | 0 | — |
| Normal kidney - HY | 1 | + | 1 | + | 1 | + | 0.1 | +/— |
| Normal kidney - ID | 1 | + | 1 | + | 1 | + | 0.5 | + |
| ERO (African green) | 10 | + | 5 | + | 5 | +/— | 0 | — |

Serological specificity of anti-gp130 monoclonal antibodies. Mouse monoclonal antibodies were produced against the human melanoma line, SK-MEL-28, and a lectin-affinity purified membrane fraction of these cells. Eight antibody-producing clones were selected for detailed analysis (Q.14, Q.24, N.9, R.23, 846, 239, 986, 829). Clones Q14, Q24, N9 and R23 are disclosed in Dippoled, et al Supra. The serological specificity of the four new monoclonal antibodies 846, 239, 986 and 829 was determined using a panel of 80 human cell lines (40 melanomas, 7 gliomas, 12 epithelial cancers, 8 renal cancers, 4 lymphomas, 4 EBV-transformed B cell lines and 5 normal cell lines) and 4 xenogeneic cell lines (Table 1). The serological analysis revealed that these four monoclonal antibodies had reactivities similar to each other and to four previously reported antibodies.

Radioimmunoprecipitation analysis. Radioimmunoprecipitation experiments indicated that each of the eight monoclonal antibodies, with the exception of 986 and 829, precipitates a 130,000 molecular weight protein from cells radiolabeled with [$^3$H]glucosamine. The similarity in serological specificities between the 986 and 829 antibodies and the other six monoclonals show that these two antibodies were also detecting the gp130 (see Table 1), even though they are unable to efficiently immunoprecipitate it. Furthermore, subtle differences between the serological reactivities of the 986 and 829 antibodies show that they may also detect epitopes spatially distinct from one another. When the 986 and 829 antibodies are mixed in equal proportions, strong precipitation of gp130 occurs. Efficient precipitation of gp130 does not occur when either of the antibodies is used alone, even when the antibody concentration is increased as much as five-fold. Further, the precipitation of gp130 with the combination of 986 and 829 antibodies is not the result of a nonspecific reaction since mixing either antibody with an unrelated antibody does not result in strong precipitation of the gp130. Mixing either 986 and 829 antibodies with a monoclonal antibody directed against a $M_r$ 95,000 glycoprotein also present on melanoma cells results in the efficient precipitation of only the gp95. Therefore, (a) the 986 and 829 antibodies detect the same gp130 molecule and (b) these antibodies are directed against two different epitopes on the gp130. Immunodepletion experiments indicate that the other six monoclonal antibodies detect the same 130,000 molecular weight glycoprotein and not unrelated molecules of similar mass.

Epitope analysis. In order to determine the actual number of epitopes detected by the eight anti-gp130 monoclonal antibodies, two variations of competition-binding assays were used. The first is a non-radioactive assay based on antibody competition for reactive sites on the cell surface of cultured melanoma cells. The scheme of this assay is as follows: (1) First prepare F(ab')2 fragments from the 846 antibody. F(ab')2 fragments can still combine with antigen but cannot be detected by the protein A-MHA assay used as protein A requires an intact Fc portion for binding. (2) Block all the reactive sites of the gp130 antigen with a dilution series of 846 F(ab')₂ fragments. (3) Determine if any of the other intact anti-gp130 monoclonal antibodies can bind to gp130 antigen, using the PA-MHA assay. Since protein A reacts with the Fc portion of immunoglobulins, only intact gp130 antibodies which are attached to an epitope not spatially blocked by the 846 F(ab')₂ fragments will be detected.

F(ab')₂ fragments prepared from the 846 monoclonal antibody completely inhibits reactivity with the homologous intact antibody. Q.14, Q.24, 239 and 846 are effectively blocked by 846 F(ab')₂ fragments. The essentially identical characteristics of the blocking reactions indicates that these four antibodies probably detect the same epitope (determinant A). The N. 9, 986 and 829 antibodies are not blocked to any detectable degree by the 846 F(ab')₂ fragments and therefore detect epitopes spatially distinct from that defined by the 846 group. R.23 antibody appears to be partially blocked by 846 F(ab')₂ fragments and may, therefore, detect an epitope spatially closer to the A determinant. These results were confirmed using a second assay based on the ability of bound intact IgG to complete with $^{125}$I-labeled IgG monoclonal antibodies 846, Q.14, Q.24 and 239 completely inhibit binding of $^{125}$I-labeled 846 antibody whereas 829, 986 and N.9 do not. The immunoprecipitation data indicates that the 986 (determinant C) and 829 (determinant B) antibodies recognize epitopes distinct from one another The N.9 antibody appears to recognize a fourth determinant, as it is not blocked by the 846 antibody, but unlike 829 and 986, can efficiently immunoprecipitate gp130 from cell lysates. Further, N.9 antibody biosynthetically labeled with [$^{35}$S]-methionine did not block binding of non radioactive 829 or 986 antibodies. Taken together these results show that the eight monoclonal antibodies tested detect four and possibly 5, different epitopes on gp130.

Intracellular processing of the gp130 molecule. SK-MEL-28 melanoma cells were pulsed with [$^{35}$S]methionine for 15 min, then chased with non-radioactive medium for increasing periods of time. The cells were washed, lysed and immunoprecipitated with monoclonal antibody 846. After a 15 minute pulse, the only protein species specifically precipitated by 846 antibody migrated with a molecular weight of 100,000. The precursor can also be precipitated by the Q. 14, Q.24, R.23, N.9 and 239 antibodies. The 986 and 829 antibodies cannot precipitate the precursor individually but can do so if combined.

Half-life of gp130 and pr100 molecules. SK-MEL-28 cells were pulse-labeled for 15 min with [$^{35}$S]methionine, chased for increasing periods of time and then lysed and immunoprecipitated with the 846 monoclonal antibody. The precipitated radiolabeled pr100 precursor and gp130 end product were resolved on polyacrlyamide gels by fluorography. The bands were cut the number of counts were quantitated. The results of this experiment indicate that the 100 kD precursor has a half-life of 45 min, while the 130 kD end product has a half-life in excess of 12 hrs. This is in contrast to another melanoma-associated antigen, gp95, thought to be related to transferring (Brown, J. P., R. M. Hewick, I. Hellström, K. E. Hellström, R. F. Doolittle and W. J. Dreyer, 1982. Human melanoma-associated antigen p97 is structurally and functionally related to transferring Nature 296:171), which has a half-life of about 10 hrs, and whose 90 kD precursor has a half-life of 90 min.

Synthesis of precursors to gp130 in the presence of tunicamycin. Both the $M_r$ 100,000 precursor species and the final $M_r$ 130,000 product can be labeled with [$^3$H]D-glucosamine. In an effort to detect unglycosylated precursor species and to determine if the biochemical event responsible for the increase in molecular weight of the 100,000 precursor to 130,000 is the processing of N-linked oligosaccharide side chains, the antibiotic tunicamycin (TM) to inhibit nascent glycosylation. The effect of various amounts of TM on the synthesis of macromolecules in human melanoma cells was first determined. SK-MEL-28 cells were treated for five hrs with TM at concentrations ranging from 0.6 μg/ml–10 μg/ml and subsequently labeled for 60 min with either 50 μCi [$^{35}$S]-methionine or 50 μCi [$^3$H]mannose/ml in the presence of TM. FIG. 7 indicates that a dose of TM sufficient to inhibit [$^3$H]mannose incorporation 99% (2.5 μg/ml), overall protein synthesis is reduced by 23%.

SK-MEL-28 cells were subsequently incubated in the presence of 2.5 μg TM/ml for five hours then labeled for 60 minutes with 50 Ci [$^{35}$S]methionine/ml. The cells were lysed and the extracts were immunoprecipitated with anti-gp130 monoclonal serum (846). In the presence of 2.5 μg TM/ml, gp130 molecules are not produced. However, the precursor molecule pr100$^{gp}$ is evident as is a new protein with a molecular weight of 80,000. This 80 kD species may represent the primary translational product prior to any posttranslational modification. In the absence of TM or in the presence of 0.25 μg TM/ml both the intermediate precursor pr100$^{gp}$ and the final product, gp130, can be seen.

Treatment with tunicamycin inhibits incorporation of N-linked oligosaccharides, and thereby the expression of completely processed gp130 molecules. However, since TM did not completely abrogate the formation of the 100 kD precursor, the data suggested either that the concentration of TM used was insufficient to insure complete inhibition of N-glycosylation or that the pr100$^{gp}$ molecule also contains some O-linked carbohydrate chains, whole synthesis is not affected by TM.

As gp130 is also present in low amounts on some types of normal cells, it was of interest to determine if the processing of this protein was identical in both normal and malignant cells. Pulse-chase experiments were using performed short-term cultures of normal kidney epithelium from kidney biopsies. It was found that the intracellular processing of pr100$^{gp}$ to gp130 in normal kidney epithelium cells and in malignant cells was identical in all respects.

What we claim:

1. Monoclonal antibodies which specifically bind to the gp130 glycoprotein cell surface antigen of human melanoma cells, wherein said monoclonal antibodies are selected from the group consisting of monoclonal antibodies 829 and 986 produced by the hybridomas having the A.T.C.C. accesion numbers HB 8289 and HB 9721, respectively.

2. Hybridoma cell lines which produce monoclonal antibodies mAb 986 and mAb 829 and which have A.T.C.C. accession numbers HB 9284 and HB 8289, respectively.

3. Method of detecting the C determinant of the gp130 antigen on human melanoma cells comprising contacting said cell with monoclonal antibody mAb 986 under conditions favoring formation of complexes of said antigen and said monoclonal antibody and detecting formation of complexes of said melanoma cells and said monoclonal antibody.

4. Method of detecting the B determinant of the gp130 antigen on human melanoma cells comprising contacting said cell with monoclonal antibody mAb 829 under conditions favoring formation of complexes of said antigen and said monoclonal antibody and detecting formation of complexes of said melanoma cells and said monoclonal antibody.

5. Method of detecting melanoma cells in a human comprising contacting a tissue or cell sample from said human with at least one monoclonal antibody selected from the group consisting of mAb 829 and 986 under conditions favoring formation of complexes of said cell and said monoclonal antibody and detecting formation of complexes between melanoma cells and said monoclonal antibody.

6. Monoclonal antibodies of claim 1, further comprising a detectable label.

7. Monoclonal antibodies of claim 1, immobilized on a solid support.

* * * * *